(12) United States Patent
Wagner

(10) Patent No.: US 7,576,857 B2
(45) Date of Patent: Aug. 18, 2009

(54) PARTICLE COUNTER WITH LASER DIODE

(75) Inventor: Gregg A. Wagner, Boulder, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 567 days.

(21) Appl. No.: 10/923,339

(22) Filed: Aug. 20, 2004

(65) Prior Publication Data

US 2006/0038998 A1    Feb. 23, 2006

Related U.S. Application Data

(63) Continuation-in-part of application No. 10/228,577, filed on Aug. 27, 2002, now Pat. No. 6,859,277.

(51) Int. Cl.
G01N 21/00 (2006.01)

(52) U.S. Cl. .................... 356/337; 356/338

(58) Field of Classification Search ......... 356/334–343
See application file for complete search history.

(56) References Cited

U.S. PATENT DOCUMENTS

| | | | |
|---|---|---|---|
| 3,797,937 A * | 3/1974 | Shofner | 356/336 |
| 4,074,939 A * | 2/1978 | Rabl | 356/435 |
| 4,113,386 A * | 9/1978 | Lepper, Jr. | 356/338 |
| 4,596,464 A | 6/1986 | Hoffman et al. | |
| 5,092,675 A | 3/1992 | Sommer | |
| 5,262,841 A * | 11/1993 | Blesener et al. | 356/338 |
| 5,282,151 A | 1/1994 | Knollenberg | |
| 5,402,438 A | 3/1995 | Tanuma | |
| 5,459,569 A | 10/1995 | Knollenberg et al. | |
| 5,475,487 A * | 12/1995 | Mariella et al. | 356/336 |
| 5,889,589 A | 3/1999 | Sandberg | |
| 6,104,491 A * | 8/2000 | Trainer | 356/336 |
| 6,211,956 B1 * | 4/2001 | Nicoli | 356/337 |

(Continued)

FOREIGN PATENT DOCUMENTS

JP        9-113436        5/1997

(Continued)

OTHER PUBLICATIONS

British Search Report, Corresponding to Great British Application No. GB 0318240.9, Completed Dec. 15, 2003.

(Continued)

*Primary Examiner*—Michael P Stafira
(74) *Attorney, Agent, or Firm*—Greenlee, Winner and Sullivan, P.C.

(57) ABSTRACT

A liquid particle counter for optically detecting an unconstrained particle suspended in a flowing liquid includes a sample chamber having a liquid inlet and a liquid outlet; a laser diode module producing a symmetrically collimated laser beam; a beam shaping optical system directing the laser beam at the sample chamber; and an optical detector located to detect light scattered by the particle in the sample chamber, the detector producing an electric signal characteristic of a parameter of the particle. The laser beam has an energy of a watt or more and passed through an aperture in a black glass aperture element in the sample chamber. The black glass aperture element removes diffracted and stray light from the beam without damage to the sample chamber.

21 Claims, 5 Drawing Sheets

U.S. PATENT DOCUMENTS

| | | |
|---|---|---|
| 6,628,386 B2 | 9/2003 | Davis et al. |
| 6,680,800 B1 | 1/2004 | Schreiber et al. |
| 6,859,277 B2 * | 2/2005 | Wagner et al. ............. 356/337 |

FOREIGN PATENT DOCUMENTS

| | | |
|---|---|---|
| JP | 9-311103 | 12/1997 |
| JP | 10-2856 | 1/1998 |
| JP | 2000-512390 | 9/2000 |
| JP | 2002-223019 | 8/2002 |
| WO | WO 01/27686 | 4/2001 |

OTHER PUBLICATIONS

Japanese Official Action, Corresponding to Japanese Application No. 2003-303709, Mailed Mar. 31, 2009.

Ueki et al. (Jul. 1992) "Semiconductor Laser 2-Focus Velocimeter and the Application Thereof," The 29$^{th}$ Lecture Meeting of Turbomachinery Society in Toyama, Japan, Turbomachinery Society, pp. 241-244.

Ueki et al. (Dec. 25, 1992) "Measurement of Stream Using Wide-Stripe Type Semiconductor Laser," *Collection of Papers of the Japan Society of Mechanical Engineers* 58(556):171-175.

* cited by examiner

PARTICLE COUNTER WITH LASER DIODE

CROSS-REFERENCE TO RELATED APPLICATIONS

This application is a continuation-in-part of U.S. patent application Ser. No. 10/228,577 filed Aug. 27, 2002, now U.S. Pat. No. 6,859,277.

BACKGROUND OF THE INVENTION

1. Field of the Invention

The invention in general relates to systems which utilize light scattering principles to detect and count undesirable single particles in fluids, referred to in the art as light scattering particle counters, and more particular to such a particle counter that utilizes a laser diode light source.

2. Statement of the Problem

Particle counters are used to detect and measure the size of individual particles suspended in a fluid. Each particle that is detected is counted, and an indication of the number of particle counts within a channel, with each channel corresponding to a particular size range, is provided. For particle counters to operate effectively, the density of particles in the fluid must be very small—indeed, the particles are generally considered to be contaminants. It is important to distinguish the science of particle counting from other scientific fields, such as photometry and cytometry, which also utilize scattered light, but in which the density of the particles in the fluid is relatively large; often it is the particles of the fluid itself that are detected and analyzed. These latter systems rely on collecting scattered light from thousands, millions, and even billions of particles; therefore, their principles of operation are very different from the principles used in particle counters.

Particle counters are generally used to detect contaminants in extremely pure fluids, such as those used in high tech electronics and the pharmaceutical industry. Generally, small samples of the fluids used in the manufacturing processes are diverted to the particle counters, which sound an alarm if the number and/or size of the particles detected is above a predetermined threshold. Since a small sample of the manufacturing fluid is generally not completely representative of the entire volume of the manufacturing fluid, statistics is used to extrapolate the state of the manufacturing fluid from the sample. The larger the sample, the more representative it is, and the more quickly an accurate determination of the number and size of particles in the manufacturing fluid can be made. It is desirable for a particle counter to detect particles as small as possible, as fast as possible, in as large a sample as possible.

Physical constraints require tradeoffs between the above goals. For example, sample volume and speed usually must be sacrificed to detect smaller particles. This is a direct result of the fact that, for particles to be detected in a particular fluid, the fluid must be constrained to flow through the monitoring region of a particle counter. Physical objects, such as nozzles and flow tubes, must be used to direct the fluid flow to the particle counter monitoring region. If it is desired to detect the particles in the entire sample flow, then scattered light from the entire sample flow must be collected. This generally results in light scattered from the physical constraining objects, such as a nozzle or flow tube, also being collected, which light creates noise in the output. The noise prevents detection of extremely small particles. This noise can be avoided by detecting particles in only a small portion of the sample flow. Particle counters that attempt to count all the particles in a fluid sample are generally referred to as volumetric particle counters, and particle counters that detect particles in only a small portion of the fluid flow are generally referred to as in-situ particle counters.

The word in-situ in Latin literally means in the natural state. That is, ideally, it refers to measurements unaffected by the measurement instrumentation. In an in-situ system, to be unaffected from the constraining elements, the detected particles must be far from the constraining elements, and only particles in a small fraction of the sample fluid flow are detected. In-situ systems commonly process 5% or less of the sampled fluid. As a result of measuring only a selected fraction of fluid flow, however, in-situ systems take more time to achieve a statistically significant determination of the fluid cleanliness level or fluid quality. When measuring particle contamination levels in a clean room environment, this extended measurement time generally incurs the risk that an unacceptably high level of airborne or liquid particle concentration could go undetected for substantial time periods, thereby allowing a large number of manufactured parts to be produced under unacceptably "dirty" conditions. This situation can lead to substantial economic loss owing to the waste of time and production materials in the affected facility.

Since it is practically impossible to actually measure 100% of the particles carried by flowing fluid, herein the term "volumetric" generally corresponds to systems which measure 90% or more of the particles flowing through a measurement device. Volumetric particle measurement systems generally provide the advantage of measuring a greater volume of fluid, whether liquid or gas, within a fixed time period, thereby enabling a more rapid determination of a statistically significant measure of fluid quality. In the case where the particle concentration exceeds a predetermined permissible limit, this more rapid fluid processing generally enables a defective manufacturing process to be halted more quickly and more economically than would be possible employing in-situ measurement systems. However, as indicated above, volumetric measurement systems generally experience more noise than do in-situ systems because the efforts expended to control the location and flow characteristics of the fluid being analyzed generally perturbs the characteristics being measured to a greater extent than does in-situ measurement.

In various circumstances, there may be measurement processes having characteristics which are intermediate between in-situ and volumetric processes. Thus, where in-situ measurement generally corresponds to particle measurement within 5% or less of fluid transported through a measurement device, and volumetric measurement generally corresponds to analysis of 90% or more of such fluid, it will be recognized that measurement processes may be configured to process 10%, 30%, 50%, or other percentages in between the levels associated with in-situ and volumetric operation. Accordingly, herein, the term "non-in-situ" measurement generally corresponds to measurement of a proportion of fluid equal to more than 5% of total fluid flow.

In the field of particle counting, the use of high power illumination generally enhances particle detection. Specifically, higher power levels generally enable the detection of smaller particles than lower power systems. Higher power levels also generally permit particles of a given size to be detected more quickly. Thus, high power lasers are generally used as the light source in particle counters.

Diode lasers have recently been incorporated into particle counters because of their relatively small size, economy and reliability. However diode particle counters have an inherent limitation for use in particle counters that limits their power. The power of diode lasers increases with the size of radiating surface. However, as the size of the radiating surface increases transverse radiation modes increase. FIG. 1 shows the radiation patterns, looking into the laser, for various transfers modes. As can be seen, the radiation in the fundamental transverse electromagnetic mode, designated as $TEM_{00}$, is compact and concentrated in the center. In the other modes a significant portion of the light is contained in zones separated from and some distance from the center of the beam. In certain applications, such as fiber optics, these features of the non $TEM_{00}$ modes are not a problem because multiple reflections from the sides of the fiber contains the radiation in a compact space. However, in particle counters, these modes scatter and reflect from the parts of the system constraining the fluid flow and create noise which interferes with the detection of particles and places a lower limit on the size of the particles that can be detected. Thus, particle counters that use laser diodes generally limit the mode to the $TEM_{00}$ mode, which however limits the amount of power of the diode, because, as indicted above, higher power requires a larger radiating surface, which inherently creates non $TEM_{00}$ modes.

The problems with using high power diodes are particularly acute in particle counters that detect single particles in liquids, referred to herein as "liquid particle counters". While gases will remain collimated in constraint-free jets for at least a distance necessary to pass the jets through a laser beam, liquids resist such collimation. Thus, in particle counters, liquids must be constrained by the physical walls of flow cells, and the laser beam must thus pass through the flow cell. The non $TEM_{00}$ transverse modes scatter and reflect from the flow cell walls creating noise. In addition, bubbles in the fluid, which are often present at start-up, diffract the light from all the modes. If lasers having a power of one watt or greater are used in a liquid particle counter, the heat from the combination of the non $TEM_{00}$ mode scattering and the diffraction from a bubble will damage the flow cell. Thus, all known commercial liquid particle counters that utilize laser diodes to detect and measure single particles in fluids have, up until now, been limited to single mode systems, typically the $TEM_{00}$ mode, and thus limited to less than 1 watt in power.

Accordingly, there is a need in the art for a particle counter system and method, particularly a liquid particle counter system and method, which provides high power illumination in a low noise environment and which produces a scattered light energy spectrum which is readily convertible into particle measurement data. Further, to accomplish this in a non-in-situ system would be highly advantageous.

SUMMARY OF THE INVENTION

The present invention advances the art and helps to overcome the aforementioned problems by providing a liquid particle counter utilizing a laser diode which provides a high power beam in a low noise system for rapid detection and measurement of small particles. Preferably, the beam is symmetrically collimated and has a power of a watt or more. Preferably the beam is passed through apertures that remove most of the diffracted and stray light inherent in high power symetrized laser beams. One aspect of the invention provides a glass or crystalline aperture element in the sample chamber wall which blocks diffracted and stray light without being damaged by the high power laser beam.

The invention provides a device for optically detecting an unconstrained particle suspended in a flowing liquid, the device comprising: a sample chamber having a liquid inlet and a liquid outlet; a laser diode module producing a symmetrically collimated laser beam; a beam shaping optical system directing the laser beam at the sample chamber; and an optical detector located to detect light scattered by the particle in the sample chamber, the detector producing an electric signal characteristic of a parameter of the particle. Preferably, the device is a non-in-situ particle counter. Preferably, the device is a volumetric particle counter. Preferably, the device is an in-situ particle counter. Preferably, the sample chamber includes a glass or crystalline aperture element having an aperture and the beam shaping system directs the laser beam through the aperture. Preferably, the glass or crystalline aperture element is made of black glass or light-absorbing crystalline material. Preferably, the glass or light-absorbing crystalline aperture element is made of NG1 glass or black diamond. Preferably, the device includes a light baffle chamber, and the glass aperture element is located between the light baffle chamber and the sample chamber. Preferably, the light baffle chamber is fluidly connected to the inlet and outlet to permit the liquid to flow through it. Preferably, the laser beam has an energy of one watt or greater. Preferably, the laser diode module a unique m.o.d.e.™ laser diode module. Preferably, the beam shaping optics includes an aperture system blocking a third or more of the power of the laser beam.

In another aspect, the invention provides a particle counter for optically detecting an unconstrained particle suspended in a flowing liquid, the particle counter comprising: a sample chamber having a liquid inlet and a liquid outlet, the sample chamber having a plastic wall; a glass or crystalline aperture element having an aperture and located in the plastic sample chamber wall; a laser diode module producing a laser beam; a beam shaping optical system directing the laser beam through the aperture into the sample chamber; and an optical detector located to detect light scattered by the particle in the sample chamber, the detector producing an electric signal characteristic of a parameter of the particle. Preferably, the glass or crystalline aperture element is made of black glass or black crystal.

In a further aspect, the invention provides a device for optically detecting an unconstrained particle suspended in a flowing liquid, the device comprising: a sample chamber having a liquid inlet and a liquid outlet; a laser diode module producing a laser beam having an energy of one watt or greater; a beam shaping optical system directing the laser beam at the sample chamber; and an optical detector located to detect light scattered by the particle in the sample chamber, the detector producing an electric signal characteristic of a parameter of the particle.

The invention also provides a method of detecting an unconstrained particle in a flowing liquid, the method comprising: flowing the liquid containing the unconstrained particle; providing a laser diode module producing a symmetrically collimated laser beam; directing the laser beam at the liquid flow; collecting light scattered by the particle in the liquid; and providing an output based on the collected light scattered by the particle detected in the flowing liquid. Preferably, the flowing comprises flowing the liquid through a sample chamber having a glass or crystalline aperture element having an aperture; and the directing comprises directing the laser beam through the aperture. Preferably, the method further comprises cooling the glass or crystalline aperture element with the fluid flow.

In an additional aspect, the invention provides a method of detecting an unconstrained particle in a flowing liquid, the method comprising: flowing the liquid containing the unconstrained particle; providing a laser diode producing a laser beam of one watt or more; directing the laser beam at the liquid flow; collecting light scattered by the particle in the liquid; and providing an output based on the collected light scattered by the particle detected in the flowing liquid. Preferably, the flowing comprises flowing the liquid through a sample chamber having a glass or crystalline aperture element having an aperture; and the directing comprises directing the laser beam through the aperture. Preferably, the method further comprises cooling the glass or crystalline aperture element with the fluid flow.

In yet another aspect, the invention provides a method of manufacturing a liquid particle counter, the method comprising: providing a plastic sample chamber having a black glass or black crystalline aperture element having an aperture; flowing a liquid containing an unconstrained particle through the sample chamber; providing a laser beam; directing the laser beam through the aperture; collecting light scattered by the particle in the liquid; and providing an output based on the collected light scattered by the particle detected in the flowing liquid. Preferably, the method further comprises cooling the glass or crystalline aperture element with the fluid flow.

In still another aspect, the invention provides a device for optically detecting an unconstrained particle suspended in a flowing fluid, the device comprising: a fluid inlet for producing a fluid flow; a laser diode module producing a symmetrically collimated laser beam; a beam shaping optical system directing the laser beam at the fluid flow; and an optical detector located to detect light scattered by the particle in the fluid flow, the detector producing an electric signal characteristic of a parameter of the particle.

The invention also provides a method for optically detecting an unconstrained particle suspended in a fluid, the method comprising: flowing the fluid containing the unconstrained particle; providing a laser diode module producing a symmetrically collimated laser beam; directing the laser beam at the fluid flow; collecting light scattered by the particle in the fluid; and providing an output based on the collected light scattered by the particle detected in the flowing fluid.

The invention enables much larger, and therefore more powerful, laser diodes to be used effectively in a particle counter, particularly a liquid particle counter. As will be seen in more detail below, the invention teaches how to control block diffracted and stray light created in symetrizing the beam while examining a large portion of the fluid flow. While the system permits high-powered, low noise, volumetric liquid particle counters that were not previously possible, it should be understood that the invention is not limited to volumetric systems. The invention can be used to advantage in any liquid particle counter, including non-in-situ and in-situ systems. In some aspects the invention can be incorporated into any fluid particle counter. The above and other advantages of the present invention may be better understood from a reading of the following description of the preferred exemplary embodiments of the invention taken in conjunction with the drawings in which:

DETAILED DESCRIPTION OF THE PREFERRED EMBODIMENT

In this disclosure, the term light is not limited to visible radiation but is used in a broad sense meaning any electromagnetic radiation. Stray light includes any light that is not wanted; i.e., light that is not light scattered from particles but which can get into the collection optics. Multiply reflected light is a significant source of stray light in a particle counter. That is, light that is reflected once, scattered from a scattering source, or diffracted by a lens or aperture can usually be blocked out by other apertures or absorbing black walls because the source of the unwanted light is. However, multiple reflections make it difficult to determine the direction of the light, and thus often cannot be apertured or otherwise blocked out. The terms in-situ and volumetric are used as described in the Background Of The Invention above. It is also noted that this disclosure is limited to fluid particle counters, which is a term of art. There are particle counters that detect particle counters in a vacuum. Because there is no fluid present, or rather any fluid present is rarified as compared to normal fluids, problems associated with fluid flow, light scattering from the fluid and the apparatus used to control the fluid flow are absent and the physics of such particle counters is significantly different than that of fluid particle counters. Further, it should be noted that particle counters as disclosed herein are designed to be able to detect single particles which are unconstrained in a flowing fluid as distinguished from other systems that detect and analyze the particles of the fluid itself, clouds of particles suspended in a fluid, or particles which are constrained in the fluid, such as constrained to flow in a single line past a light beam. Those skilled in the art recognize that it is a much more difficult task to detect and size single particles flowing unconstrained in a fluid; therefore, the art of particle counting involves different technology than these other particle detection and analysis systems.

Figure 4:
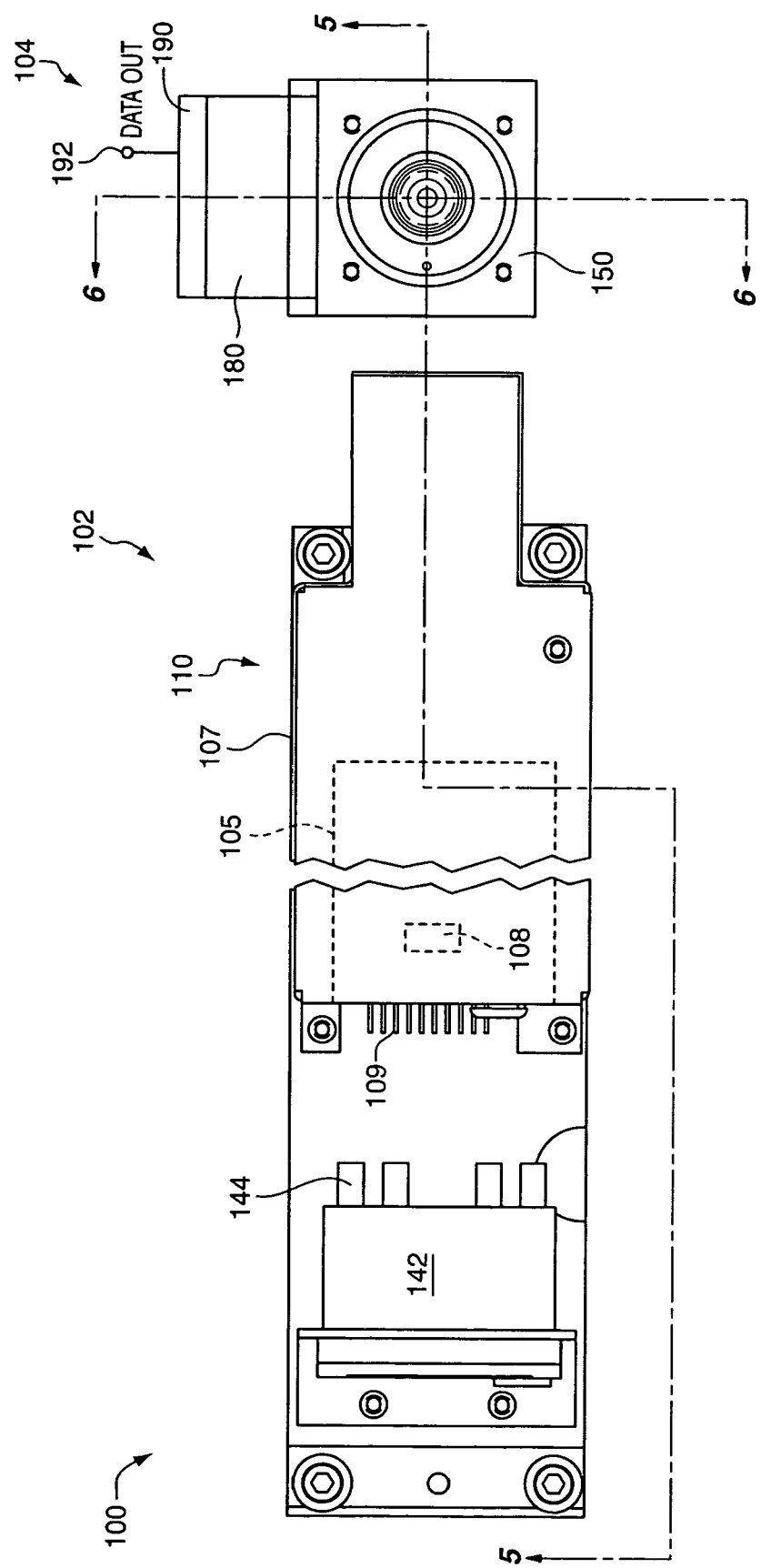
FIG. 4 is a top view of a particle counter according to a preferred embodiment of the present invention.
Figure 5:
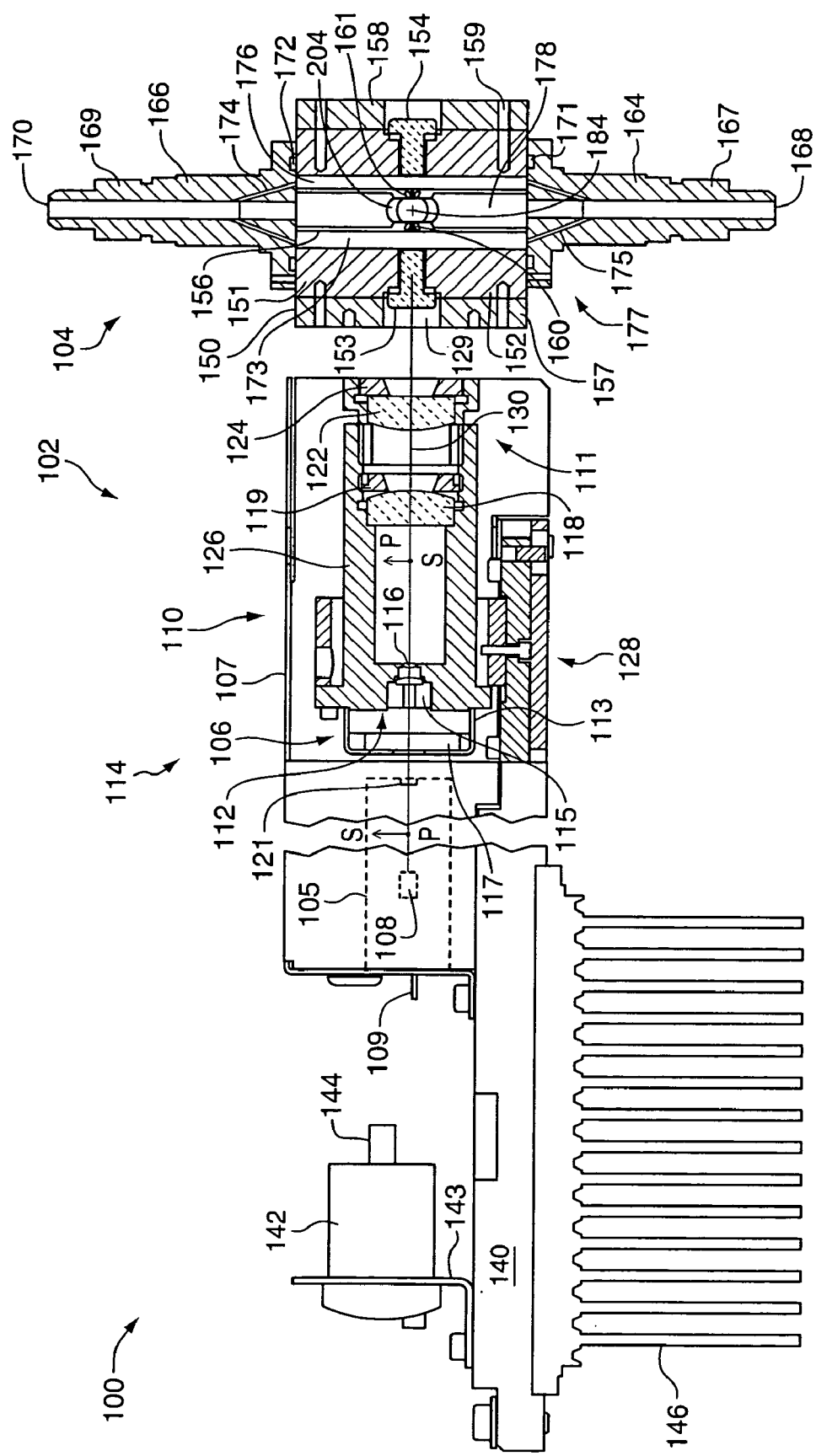
FIG. 5 is a partially plan and partially cross-sectional view of the particle counter of FIG. 4 taken through the line 5-5 of FIG. 4.
Figure 6:
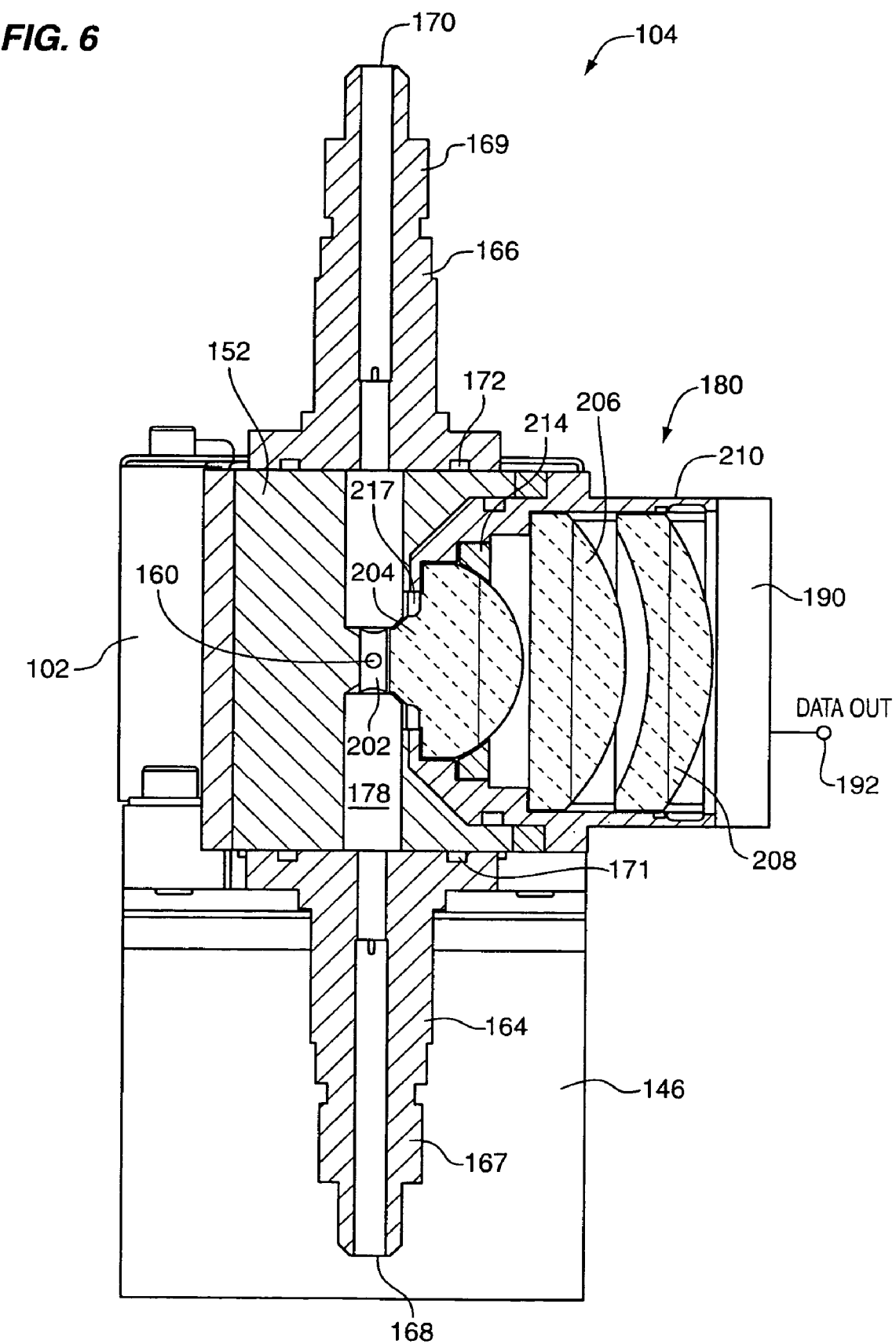
FIG. 6 is a cross-sectional view of the particle counter of FIG. 4 taken through the line 6-6 of FIG. 4.

FIG. 4 is a top view of a particle counter 100 according to the invention, FIG. 5 is a partially plan and partially cross-sectional side view taken through the line 5-5 of FIG. 4, and FIG. 6 is a cross-sectional view taken through the line 6-6 of FIG. 4. Particle counter 100 is shown with a break in FIGS. 4 and 5 so as to better fit in on the drawing without altering the scale significantly, except as mentioned below. Particle counter 100 includes a laser assembly 102 and a flow cell and detection optics assembly 104. Laser assembly 102 includes laser module 105 and a beam shaping optics system 114 including polarization rotation unit 106, beam expander 110, and focusing optics 111, all within a housing 107. Laser assembly 102 also includes timer 142, laser base plate 140 and heat sink 146. Timer 142 is mounted on a bracket 143 and includes an electrical connector 144 for connecting it to the particle counter system electronics. Laser assembly module 105 includes strip diode laser 108 and electronics connector pins 109. Polarization rotator 106 includes half-wave plate 117 and half-wave plate support 113. Beam expander 110 includes entrance aperture element and lens retainer 115, negative lens 116, positive lens 118, lens retainer and exit aperture element 119, focusing lens 122, and lens retainer and aperture element 124, all of which are supported and held in place by optics support 126. Suitable adjusting mechanisms 128 are provided as known in the art to align and adjust the various optics elements.

Flow cell and detection optics assembly 104 includes flow cell 150, inlet assembly 164, outlet assembly 166, collection optics assembly 180, and detector 190. Flow cell 150 includes flow enclosure 151 having a wall portion 152 and a light baffle portion 156, entrance window 153, exit window 154, window retainers 157 and 158, window retainer fasteners 159, main flow volume entrance aperture element 160 and main flow volume exit aperture element 161. Inlet assembly 164 includes inlet connector 167 having an inlet passage 168 and auxiliary outlet channel 175, and outlet assembly 166 includes outlet connector 169 having an outlet passage 170 and an auxiliary outlet channel 174. O-ring 171 seals the interface between inlet connector 167 and flow cell enclosure 151, and O-ring 172 seals the interface between inlet connector 169 and flow cell enclosure 151. Baffle 156 separates the flow volume 177 into an auxiliary flow volume 173 in light baffle chamber 176 and an inner main flow channel volume 178. Aperture elements 160 and 161 fit into cup-shaped openings in baffle 156, and are held in place with an epoxy cement. Auxiliary inlet channel 175 is in fluid communication with baffle chamber 176 which is in fluid communication with auxiliary outlet channel 174. As shown in FIG. 6, main flow volume 178 narrows to a capillary sample chamber 202 in the center of the flow cell, in which capillary sample chamber 202 the laser beam 130 (FIG. 5) intersects the fluid flow and particles in the liquid scatter light which is collected by lenses, of which only the first lens 204 is visible in FIG. 5, and particle measurement and counting occurs.

Collection optics 180 (FIG. 6) includes lenses 204, 206, and 208, lens housing 210, lens retainer ring 214 and seals, such as 217.

Figure 7:
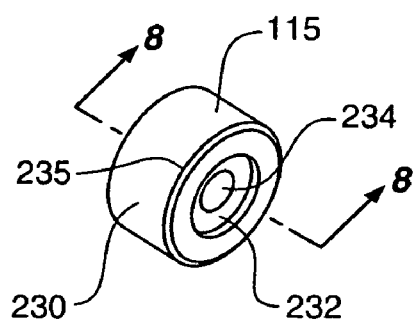
FIG. 7 is a perspective view of the entrance aperture element and negative lens retainer of the particle counter of FIG. 4.
Figure 8:
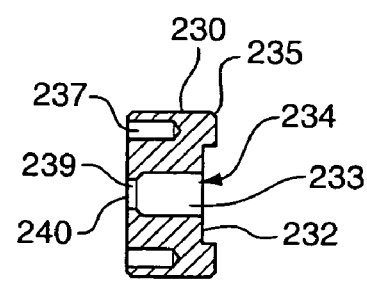
FIG. 8 is a cross-sectional view of the beam expander entrance aperture element and negative lens retainer of FIG. 7 taken through the line 8-8 of FIG. 7.
Figure 9:
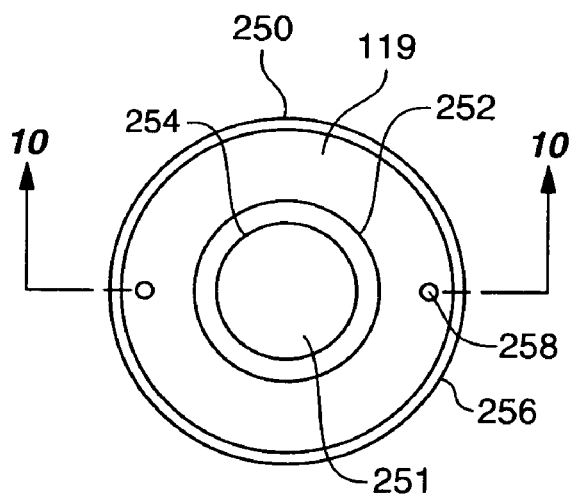
FIG. 9 is an end view of the beam expander exit aperture element and positive lens retainer of the particle counter of FIG. 4.
Figure 10:
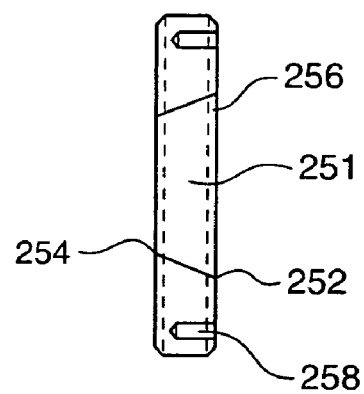
FIG. 10 is a cross-sectional view of the beam expander exit aperture element and negative lens retainer of FIG. 9 taken through the line 10-10 of FIG. 9.

A perspective view of the preferred embodiment of beam expander entrance aperture and lens retainer element 115 is shown in FIG. 7, and a cross-sectional view taken through the line 8-8 is shown in FIG. 8. Aperture and lens retainer element 115 preferably comprises a cylinder 230 having a cylindrical bore 234. At the left end in FIG. 8, the bore 234 is slightly smaller to form entrance aperture element 240, and at the right end in FIG. 8 the bore 234 is enlarged to form a lens cup 232. Holes 237 receive screws to hold the aperture and lens retainer element 115 to support 126. Preferably, cylinder 230 is 0.220 inches long (the horizontal direction in FIG. 8) and 0.400 inches in diameter, aperture element 240 is 0.067 inches in diameter and 0.02 inches deep, central portion 233 of bore 234 is 0.109 inches in diameter, and lens cup 232 is 0.228 inches in diameter and 0.030 inches deep. Both ends of cylinder 230 are chamfered, as at 235. An end view of beam expander exit aperture and lens retainer element 119 is shown in FIG. 9, and a cross-section taken through lines 10-10 of FIG. 9 is shown in FIG. 10. Expander exit aperture and lens retainer element 119 is preferably a cylinder 250 having a bore 251 shaped like a frustum of a cone with a smaller diameter 254 at its end toward laser 105 and a larger diameter 252 at its other end. It also includes screw holes 258 and its ends, such as 256 are chamfered. Preferably, cylinder 250 is 1.750 inches in diameter and 0.150 inches thick (the horizontal direction in FIG. 10). Preferably, small diameter 254 is 0.354 inches in diameter, and large diameter 252 is 0.460 inches in diameter. Lens retainer and aperture element 124 is preferably identical to lens retainer and aperture element 119.

Figure 11:
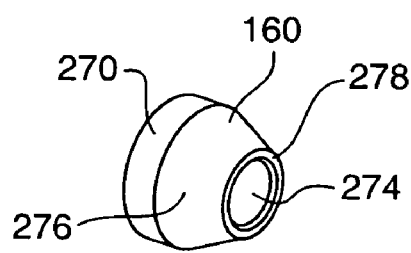
FIG. 11 is a cross-sectional view of the flow cell aperture element of the particle counter of FIG. 4.
Figure 12:
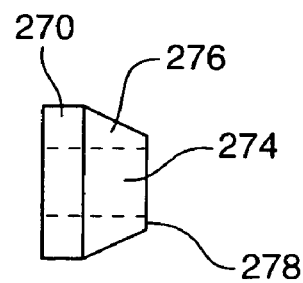
FIG. 12 is a side view of the flow cell aperture element of FIG. 11.

Flow cell entrance aperture element 160 and flow cell exit aperture element 161 are preferably identical and are shown in perspective in FIG. 11 and in a side view in FIG. 12. Aperture element 160 preferably includes a cylindrical portion 270 and a portion 276 shaped like a frustum of a cone and having a cylindrical aperture 274. Preferably, the length of aperture element 160 in the horizontal direction in FIG. 12 is 2.08 mm and its aperture 274 is 1.4 mm in diameter. Preferably, cylindrical portion 270 is 3.18 mm in diameter and 0.81 mm thick. Preferably, the outside diameter of the small end 278 of conical portion 276 is preferably 1.98 mm. Flow cell aperture elements 160 and 161 are preferably made of NG1 black glass, with the outer surfaces ground fine and the inner and end surfaces polished, though other materials may be used. For example, any light-absorbing and heat resistant flow cell material commonly used in the liquid particle counter art such as quartz, diamond, sapphire, or other light-absorbing, durable and heat resistant crystalline material may be used. Preferably, aperture and lens retainer elements 115, 119, and 124 are made of black anodized aluminum, though other non-reflective solid materials may be used. Flow enclosure 151 and window retainers 157 and 158 are preferably made of black Kel-F plastic. Windows 153 and 154 are preferably made of clear fused silica or sapphire, though any other essentially transparent material may be used. Preferably, laser module 105 is a model UM4200/M20/CB/TEC laser package made by unique m.o.d.e. AG, Jena, Germany, though any diode laser having a power of one watt or greater may be used. The unique m.o.d.e. laser is described in U.S. Pat. No. 6,680,800 issued Jan. 20, 2004 on an invention of Peter Schreiber and Thilo von Freyhold and is discussed in Thilo von Freyhold and Thomas Wittschirk, "Powerful Laser Diodes Become High-Brightness Laser Tools", *Photonics Showcase*, pp. 5-6, November 2002, both of which references are hereby incorporated by reference to the same extent as though fully disclosed herein. As known in the art, beam expander 110 includes a negative lens 116 and a positive lens 118. Negative lens 116 is preferably a F? lens while positive lens 118 is a 40 mm F4.7 lens. Focusing lens 122 is preferably also a 40 mm F4.7 lens and is ? cm thick. Preferably, aperture element 115 is preferably located ? cm from the beam exit of laser module 105, the concave surface of negative lens 116 and the convex surface of positive lens 118 are spaced ? cm apart, and the convex surfaces of lenses 118 and 122 are ? cm apart. The center 184 of flow cell 150 is placed at the waist of the expanded and focused laser beam. As known in the art, the precise positions of the optical elements are preferably adjusted to maximize the accuracy of the particle count.

The other elements of particle counter 100 for which details of dimensions, materials and/or manufacturer and part numbers are not given above or below are known in the art and thus will not be discussed in detail herein.

The invention operates as follows. A source of liquid, such as de-ionized water from a semiconducting manufacturing operation, is connected to inlet 167 and the outlet is connected back into the manufacturing liquid loop or to a waste line. A small portion of the liquid passes from inlet, through auxiliary inlet channel 175 to light baffle chamber 176 and then to auxiliary outlet channel 174 to outlet 174. Just enough liquid flows in the auxiliary route to keep any particles from settling in the light baffle chamber 176. Most of the liquid flows into main flow volume 178 and through capillary 202. Because the pressure difference between the baffle chamber 176 and the sample chamber 202 is relatively small, and especially because aperture 274 is very small compared to the size of the baffle chamber 176 and the main sample chamber 202, negligible fluid flows through aperture 274 of aperture elements 160 and 161. Laser beam 130 is generated at the exit window of laser package 105. The beam as generated has the S electromagnetic vector in the vertical direction in FIG. 5 and the polarization (P) vector out of the paper in FIG. 5. Half-wave plate rotates the beam so that the polarization is in the vertical direction in FIG. 5 and the S vector is into the paper. The beam shaping optics system 114 comprising half-wave place 117 and lenses 116, 118, and 122 is placed so that the focal plane of the system is located on the exit window 121 of laser module 105. As described in the references cited above, the optics of the preferred unique m.o.d.e. transforms the laser diode emitter into a square virtual emitter. The beam of the preferred unique m.o.d.e. laser is symmetrically divergent and preferably has an essentially square focus and an essentially square far field, with equal quality in the fast and slow axes. The divergence angle of the unique m.o.d.e. laser is approximately 8 milliradians, which corresponds to a beam quality of $M_x^2 \approx M_y^2 \leq 20$. However, the optics also creates a large amount of diffracted radiation at the edges of the beam. Entrance aperture element 115 removes most of this diffracted radiation and leaves just the essentially uniform beam center. Diffractions and stray light due to entrance aperture element 115 and beam expander optics 110 are removed by aperture element 119, while diffractions and stray light from aperture element 119 and focusing lens 122 are removed by aperture element 124. Recessed window opening 129 further removes diffractions and stray light from the earlier structures. Diffractions and stray light from windows 153 and 154 and other parts of the flow cell are trapped and absorbed in light baffle chamber 176. Glass aperture elements 160 and 161 block and absorb diffractions and stray light from laser beam 130 and from other sources in the particle counter system. Laser beam 130 passes through aperture 274 in aperture elements 160 and 161. Particles in liquid passing through the capillary 202 scatter the light from the laser beam 130, a portion of which scattered light is collected by collection optics 180 and directed to detector 190. As known in the art, detector 190 is preferably a photo detector which produces an output data signal on output 192, which output signal is representative of the number and size of particles detected by the particle counter 100. The data signal may be processed by electronics that form part of the particle counter 100, but more often is processed by a computer system (not shown) which stores and presents the data in forms desired by the user.

Figure 1:
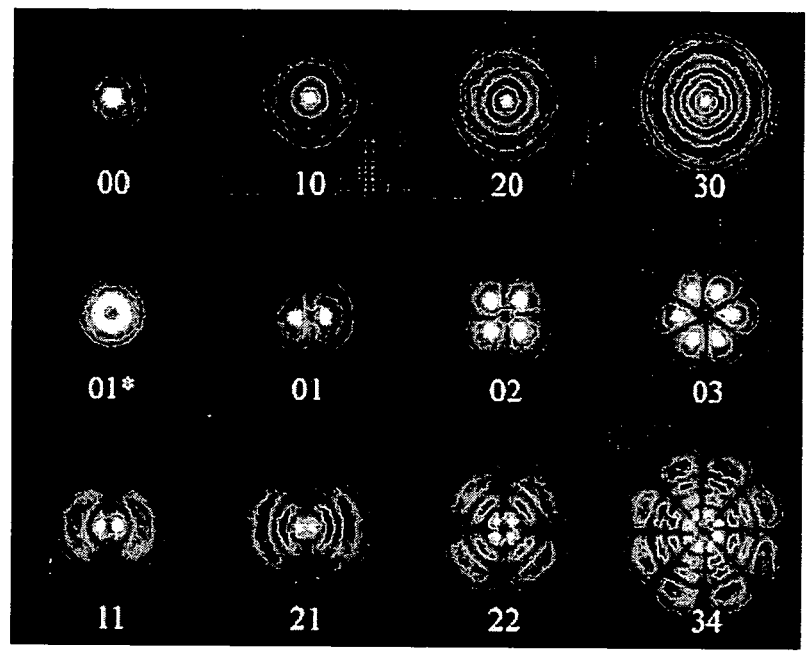
FIG. 1 shows the radiation pattern for twelve different modes of a high power diode laser.
Figure 2:
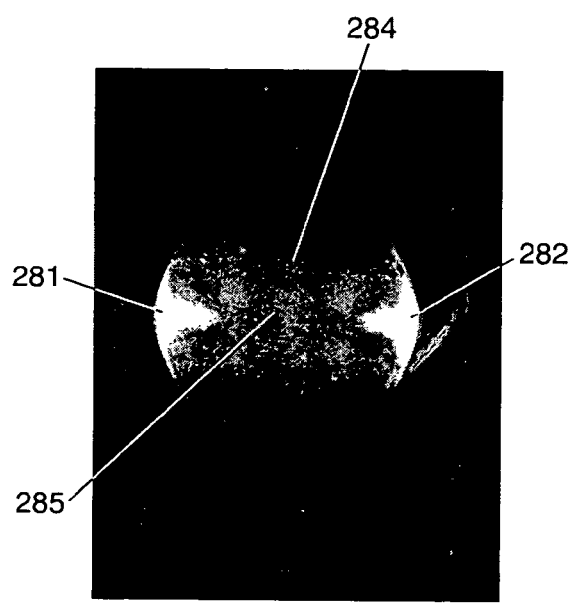
FIG. 2 is a depiction of a photograph of a laser beam passing through the flow cell of the particle counter according to the invention without the black glass aperture element.

A key aspect of the invention is that laser 105 is a strip laser diode which produces much more power than any laser diode used in prior art liquid particle counters. In FIG. 4, laser diode 108 is being viewed from the long "strip" side and its size is exaggerated; otherwise, it would be difficult to show clearly. Preferably, the length of strip laser diode 108 in the vertical direction in FIG. 2 is 100 microns or more, while the width extending into and out of the paper is 1 micron (the vertical direction in FIG. 5), though the invention contemplates that other sizes of strip laser diodes may be used. To develop significant power, at least one dimension of the laser diode should be 10 microns or greater, and more preferably 50 microns or greater. Most preferably, it is 100 microns or greater. The strip laser diode according to the invention has a power of 1 watt or greater, and more preferably 2 watts or greater. As indicted above, the preferred laser is the unique m.o.d.e. symetrically collimated laser. This laser has a center wavelength of 808 nanometers, though other wavelengths may be used. Preferably, a laser of from 1 watt to 5 watts of power is used in particle counter 100 according to the invention.

Figure 3:
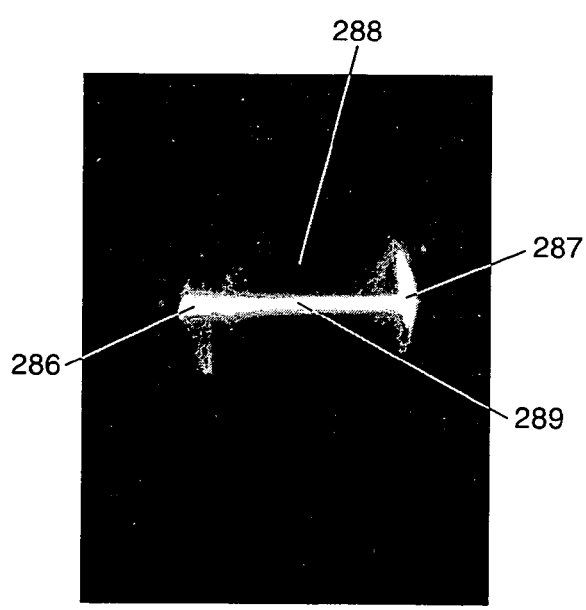
FIG. 3 is a depiction of a photograph of a laser beam passing through the flow cell of the particle counter according to the invention with the black glass aperture element.

An important aspect of the invention is the black glass aperture elements 160 and 161. FIG. 2 is a depiction of a photograph of the laser beam 130 passing through capillary 202 without the aperture elements 160 and 161. As can be seen, there is a large amount of scattered light 281 and 282 generated at the fluid/glass interfaces, as well as a large amount of stray light 284, that probably originates at the interfaces. FIG. 3 is a depiction of a photograph of the laser beam 130 passing through the capillary 202 with the aperture elements 160 and 161 in place. As can be seen, the scattered light 286 and 287 at the interfaces as well as the stray light 288 is much less. The important aspect to compare is the apparent intensity of the laser beam at 285 and 289. The laser beam 289 is much brighter, with the laser beam 285 nearly washed out by the stray light 284. It is important to keep in mind that FIGS. 2 and 3 only show the relative intensities of the scattered light and stray light to the laser beam in the same picture (comparing 281, 282, and 284 to 285 and comparing 286, 287 and 288 to 289). That is, the camera taking the picture adjusts its aperture to the high intensity of the scattered light in FIG. 2, which washes out the less intense laser beam, while in FIG. 3 the scattered light is of less intensity than the laser beam so the laser beam is not washed out. One skilled in the art will recognize that in FIG. 2 the scattered and stray light will wash out the scattering from particles to even a greater extent, since the intensity of scattered light from the particles is much less than the intensity of the laser beam, so that the particle counter of FIG. 2 would be essentially useless, while the particle counter of FIG. 3 is able to detect particles as small as 0.05 microns at flow rates of 1000 ml/minute.

Another important advantage of the glass aperture elements 160 and 161 is their ability to withstand significant heating. Without the glass aperture elements, the heating due to the large amount of diffracted radiation in the symmetrically collimated beam 130 is sufficient to melt the Kel-F plastic. This is particularly true if a bubble becomes trapped in capillary 202. Such a bubble diffracts the laser light causes it to heat the flow cell even more than normal. Users are generally warned not to turn the laser on in particle counters until the liquid flow has started, to prevent damage to the flow cell, but this cannot always be counted on because particle counters are often used in high-pressure emergencies and/or by lesser skilled persons. Because of its resistance to damage from de-ionized water and other chemicals, Kel-F plastic has become the state-of-the-art in liquid particle counter flow cells. Thus, conventional liquid flow cell construction techniques are not suitable for use with high-powered lasers. Glass aperture elements 160 and 162 overcome these problems.

A related feature of the invention is the use of the glass aperture elements 160, 161 in combination with the flow cell baffle 156, and the associated outer flow channel with auxiliary volume 173 which contacts the exterior side of the glass aperture elements. This flow of fluid over the glass aperture element cools the aperture element, and further reduces the heating problems do to the high power of the laser and the diffractions associated with symmetrical collimation. The fluid in the sample chamber 202 also contacts the glass and cools it.

As suggested by the baffles 156 that separate the flow as shown in FIG. 5 and the small diameter of the aperture 274 in the glass aperture element 160, the particle counter 100 describe herein is an in-situ particle counter. It samples approximately 0.375 percent of the flow volume. However, the invention can also be used in non-in-situ particle counters, including volumetric particle counters.

Another important aspect of the invention is the use of a symmetrically collimated strip diode laser. As indicated above, the symmetrical collimation results in extensive diffraction. Up until the invention, this diffraction has resulted in such a high level of stray light, as shown in FIG. 2, that the symmetrically collimated lasers were not seen to be useful in particle counting.

The aperturing of the unique m.o.d.e. laser is another important feature of the invention. The optics 114 takes the 1.1 mm×1.1 mm cross-section of the unique m.o.d.e. laser and focuses it to a 96 micron×96 micron cross-sectional beam, i.e., a 96 $\mu m^2$ spot size. The aperturing system 112 described above creates a beam with a 43 $\mu m^2$ spot size. Preferably, aperturing system 112 blocks a third or more of the power of the laser beam, including nearly all of the original diffracted light in the beam.

Having solved the problem of employing a high-powered laser in a particle counter, numerous other advantages of the particle counter 100 have been found. To explain these advantages, we shall compare the system according to the invention to the state-of-the-art prior art particle counter using a double frequency Nd-YAG 532 nm laser. To get a comparable signal-to-noise ratio as the prior art system, it is necessary to run the unique m.o.d.e laser at 1.6 watts output. The double frequency Nd-YAG laser has a rated mean time to failure (MTTF) of 15,000 hours. This is less than two years of constant run time in most particle counter applications. The MTTF of the semiconductor laser according to the invention is 16,000 hours running at full optical output power and at 25° C. This is better than the Nd-YAG laser, but only a little. However, as indicated above, the semiconductor laser can be run at 1.6 watts for a comparable performance to the Nd-YAG laser system. The full power of the preferred semiconductor laser is 4.2 watts. This gives a power factor advantage of Operation Power/Maximum power equal to 13.4. Thus, the MTTF of the laser in the system according to the invention is 13.4×16,000 hours=24.7 years!

Another advantage is the power consumption of the system 100 according to the invention. Power consumption of the Nd-YAG laser mentioned above is typically 40 watts (W), but can be as high as 150 watts in maximum delta temperature conditions. The laser deliver 80 mW of power. Thus, it takes 40 W to deliver 80 mW of laser power. In comparison, at the 1.6 W of optical power required for a comparable result, the preferred laser consumes 6 W of power. If a thermoelectric cooler is used to cool the laser to a 20° C. delta temperature, this will consume another 7 W. Thus, it requires 13 W to deliver 1.6 W of laser power, which is much more efficient than the prior art system.

The liquid particle counter 100 according to the invention has been found to have many other advantages over the prior art liquid particle counters. It is relatively maintenance free; its power remains constant over longer periods, that is, it maintains calibration; it is easier to manufacture and calibrate; it is more reliable, enabling longer warranty periods; it is less costly to manufacture and operate; beam waist movement, and thus image movement, is greatly reduced because the solid state lasers are thermally controlled; optics design is simplified; and no frequency locking is required for solid state lasers in contrast to Nd-YAG lasers.

Another advantage of the preferred symmetrically collimated laser according to the invention is that the energy distribution across the laser beam is more uniform. In prior art cavity-type lasers, the energy distribution was essentially Gaussian, wherein in the symmetrically collimated laser the distribution is much more of a flat-topped curve with steep sides, almost a square-wave shape. The square shape results in better resolution of particle size. Also, with the prior art Gaussian energy distributions, less than 100% of particles less than about 0.117 µm in size were counted, but for particles greater than 0.117 µm in size the percentage counted was greater than 100%. That is, for larger particles, there were significant false counts. In the particle counter of the present invention, the percentage detected versus size curve is much flatter, resulting in a lower number of false counts.

There has been described a novel particle counter system that utilizes a symmetrically collimated laser diode and which permits the use of lasers of one watt or greater power in a liquid particle counter. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. For example, a wide variety of beam shaping optics 114 may be used. Mirrors may be used in place of lenses. Or, the entire flow cell 150, or at least a larger portion of it than aperture elements 160 and 161, may be made of black glass or similar material. As another example, the light collector 180 and detector 190 may be replaced with a wide variety of other collection and detection systems, ranging from a single photodetector to very complex systems using a large number of lenses and/or mirrors and/or multiple detectors and/or detector arrays. Light collection is shown as collecting scattered light in directions about a perpendicular to the laser beam 130, but, as know in the art, the light collection may also be about a direction parallel to the beam, or entirely around the scattering particle, or in any other direction. It is also evident that the methods recited may in many instances be performed in a different order; or equivalent structures and processes may be substituted for the various structures and processes described. Consequently, the invention is to be construed as embracing each and every novel feature and novel combination of features present in and/or possessed by the invention herein described.

I claim:

1. A device for optically detecting an unconstrained single particle suspended in a flowing liquid, said device comprising:
   a sample chamber having a liquid inlet and a liquid outlet, said sample chamber adapted to permit said single particle to flow essentially without constraint between said inlet and outlet;
   a laser diode module producing a symmetrically collimated laser beam having a power of one watt or more;
   a beam shaping optical system directing said laser beam at said sample chamber; and
   an optical detector located to detect light scattered by said single particle in said sample chamber, said detector producing an electric signal characteristic of a parameter of said single particle.

2. A device as in claim 1 wherein said device is a non-in-situ particle counter.

3. A device as in claim 2 wherein said device is a volumetric particle counter.

4. A device as in claim 1 wherein said device is an in-situ particle counter.

5. A device as in claim 1 wherein said sample chamber includes a glass or crystalline aperture element having an aperture and said beam shaping system directs said laser beam through said aperture.

6. A device as in claim 5 wherein said glass or crystalline aperture element is made of light-absorbing glass or light-absorbing crystalline material.

7. A device as in claim 6 wherein said glass or crystalline aperture element is made of NG1 black glass or black diamond.

8. A device as in claim 5 wherein said device includes a light baffle chamber, and said glass aperture element is located between said light baffle chamber and said sample chamber.

9. A device as in claim 5 wherein said light baffle chamber is fluidly connected to said inlet and outlet to permit said liquid to flow through it.

10. A device as in claim 1 wherein said laser diode module a unique m.o.d.e.™ laser diode module.

11. A device as in claim 1 wherein said beam shaping optics includes an aperture system blocking a third or more of the power of said laser beam.

12. A device for optically detecting an unconstrained single particle suspended in a flowing liquid, said device comprising:
    a sample chamber having a liquid inlet and a liquid outlet, said sample chamber adapted to permit said single particle to flow essentially without constraint between said inlet and outlet;
    a laser diode module producing a laser beam having a power of one watt or greater;
    a beam shaping optical system directing said laser beam at said sample chamber; and
    an optical detector located to detect light scattered by said single particle in said sample chamber, said detector producing an electric signal characteristic of a parameter of said single particle.

13. A method of detecting an unconstrained single particle in a flowing liquid, said method comprising:
    flowing said liquid containing said unconstrained particle;
    providing a laser diode producing a laser beam of one watt or more;
    directing said laser beam at said liquid flow;
    collecting light scattered by said particle in said liquid; and
    providing an output signal characteristic of a parameter of said single particle detected in said flowing liquid.

14. A method as in claim 13 wherein said flowing comprises flowing said liquid through a sample chamber having a glass or crystalline aperture element having an aperture; and said directing comprises directing said laser beam through said aperture.

15. A method as in claim 14 and further comprising cooling said glass or crystalline aperture element with said fluid flow.

16. A device for optically detecting an unconstrained single particle suspended in a flowing fluid, said device comprising:
    a fluid inlet for producing a fluid flow essentially without constraining the flow of single particles that may be in said fluid flow;
    a laser diode module producing a symmetrically collimated laser beam;
    a beam shaping optical system directing said laser beam at said fluid flow, said laser beam having a power of one watt or more; and
    an optical detector located to detect light scattered by said particle in said fluid flow, said detector producing an electric signal characteristic of a parameter of said single particle.

17. A method for optically detecting an unconstrained single particle suspended in a fluid, said method comprising:
    flowing said fluid containing said unconstrained single particle;
    providing a laser diode module producing a symmetrically collimated laser beam having a power of one watt or more;
    directing said laser beam at said fluid flow through an aperture of a glass or crystalline aperture element having an aperture;
    collecting light scattered by said particle in said fluid; and
    providing an output characteristic of a parameter of said single particle detected in said flowing fluid.

18. A method as in claim 17, wherein said glass or crystalline aperture element is made of light-absorbing glass or light-absorbing crystalline material.

19. A method as in claim 18, wherein said glass or crystalline aperture element is made of NG1 black glass or black diamond.

20. A device as in claim 1, wherein said sample chamber is made of plastic.

21. A device as in claim 12, wherein said sample chamber is made of plastic.

\* \* \* \* \*

UNITED STATES PATENT AND TRADEMARK OFFICE
CERTIFICATE OF CORRECTION

PATENT NO. : 7,576,857 B2  Page 1 of 1
APPLICATION NO. : 10/923339
DATED : August 18, 2009
INVENTOR(S) : Gregg A. Wagner It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 893 days.

Signed and Sealed this

Fourteenth Day of December, 2010

David J. Kappos
*Director of the United States Patent and Trademark Office*